United States Patent [19]

Lacks

[11] 4,413,631
[45] Nov. 8, 1983

[54] SPHYGMOMANOMETER CONSTRUCTION

[76] Inventor: Harold G. Lacks, 200 E. 64th St., New York, N.Y. 10021

[21] Appl. No.: 334,081

[22] Filed: Dec. 24, 1981

[51] Int. Cl.³ .............................................. A61B 5/02
[52] U.S. Cl. .................................... 128/677; 128/685
[58] Field of Search ...................... 128/672, 677–678, 128/684–685, 679–683, 687–690

[56] References Cited

U.S. PATENT DOCUMENTS

| | | | |
|---|---|---|---|
| 1,644,824 | 10/1927 | Feddes | 128/677 |
| 2,710,001 | 6/1955 | Freyburger | 128/681 |
| 2,952,253 | 9/1960 | Seligman et al. | 128/684 |
| 3,056,401 | 10/1962 | Greenspan et al. | 128/681 |
| 3,552,385 | 1/1971 | Janssen | 128/680 |
| 3,823,707 | 7/1974 | Hayes | 128/685 |
| 3,901,217 | 8/1975 | Clark | 128/677 |
| 3,918,436 | 11/1975 | Peart et al. | 128/677 |
| 3,929,129 | 12/1975 | Archambault | 128/677 |
| 4,007,734 | 2/1977 | Peters | 128/677 |
| 4,010,739 | 3/1977 | Leach | 128/677 |
| 4,058,117 | 11/1977 | Kaspari et al. | 128/682 |
| 4,090,503 | 5/1978 | Speidel | 128/684 |
| 4,222,390 | 9/1980 | Berliner et al. | 128/677 |

FOREIGN PATENT DOCUMENTS 135581  7/1960  U.S.S.R. ............................. 128/677

Primary Examiner—Kyle L. Howell
Assistant Examiner—Angela D. Sykes
Attorney, Agent, or Firm—McAulay, Fields, Fisher, Goldstein & Nissen

[57] ABSTRACT

The present invention relates to a sphygmomanometer construction which comprises an inflatable cuff. The cuff is adapted to encircle the human limb. Connected to the cuff is a means for inflating the cuff. A manually operable release valve is connected to the cuff so that the operator can release the pressure at a pre-determined rate. A pressure gauge is also connected to the cuff through a suitable conduit and serially connected in the conduit between the cuff and the gauge is a normally closed valve, which may be momentarily operated to the open position. In use, when the diastolic or systolic pressure is detected by means of a stethoscope or the like, the valve is momentarily operated to connect the gauge with the cuff so that the pressure will be applied to the gauge. Since the gauge is thereafter isolated from the cuff, the pressure indicated by the gauge will retain the appropriate reading.

8 Claims, 2 Drawing Figures

SPHYGMOMANOMETER CONSTRUCTION

The present invention relates to a sphygmomanometer construction which allows one taking their own or another's blood pressure to obtain a more accurate reading of the systolic and diastolic pressure readings by allowing the user to effectively isolate the individual pressure readings, thereby enabling him to observe the reading on a pressure gauge which has been frozen at the appropriate moment by the activation of a normally closed, manually operated means which serves to momentarily pressurize and subsequently isolate the said pressure gauge.

BACKGROUND OF THE INVENTION

A sphygmomanometer is a clinical apparatus for measuring the blood pressure. Such devices generally comprise an inflatable cuff which is wrapped around a human limb usually the upper arm of a patient. The cuff is usually connected by a conduit, generally rubber tubing, to a resilient hand bulb, which acts as a hand pump, and is inflated by repetitively squeezing the bulb. The cuff is connected to a pressure-indicating manometer device or pressure gauge which has a pressure-calibrated dial and a pressure needle, which is movable over the latter. The pressure gauge needle is operatively connected by a conduit, also usually rubber tubing, to the cuff, and is movable in response to changes in air pressure in the cuff. A manually operable bleeder valve, or other pressure relief device, is provided to slowly bleed air from the inflated cuff. In use, sufficient pressurized air is pumped into the inflatable cuff until the inflated cuff tightens sufficiently to occlude the brachial artery in the upper arm, i.e., stop the blood flow therein. A stethoscope is applied over the artery below the cuff, and air is gradually allowed to escape through the bleeder valve from the cuff until a pulsing rush of blood can be heard. The pressure needle on the gauge at this point indicates the systolic pressure or the highest pressure in the arteries during contraction of the heart.

As deflation of the cuff continues, the air pressure within the cuff falls, and the needle successively indicates lower and lower pressure readings. The diastolic pressure, or lowest pressure in the artery during diastole, or relaxation of the heart muscle between beats, is indicated by the needle on the dial when the last sound of the disappearing pulse is heard, i.e., when the rush of blood becomes inaudible. Upon further deflation of the cuff, the needle would normally return from its previous measurement position to its starting position. The normal systolic reading of an adult varies from 110 to 130 or 140 mm Hg. Normal diastolic readings vary from 60 to 90 mm Hg.

It is often difficult for an individual taking his own blood pressure or, for that matter, taking another's pressure, to accurately read and note the systolic and diastolic blood pressures during the blood pressure measurement due to the fact that the individual must simultaneously regulate the air bleeder valve, carefully observe the pressure needle as it quickly moves over the dial, and listen to the sounds of the pulses through the stethoscope. Moreover, even skilled personnel, who are trained in the art of taking blood pressure measurements, must either make a mental or very rapid written note of the systolic pressure reading at the appropriate time before the time approaches when the diastolic pressure must be read.

In order to eliminate the drawbacks involved in reliance upon a faulty memory and/or in making very hasty written, and possibly illegible, notes of the systolic and diastolic blood pressure readings, the prior art has proposed automatically-operated sphygmomanometer gauges which have two recording needles in addition to the main pressure needle. The main pressure needle, according to one proposal, automatically carries the two recording needles over the dial until the user decides to manually lock the respective recording needles in position. The prior art has also proposed a pair of recording needles which are moved automatically in response to pressure and electrical pulses and are locked automatically in their measured positions by a ratchet-pawl-solenoid. Examples of such automatically-operated sphygmomanometer gauges can be had by reference to U.S. Pat. Nos. 3,901,217 and 3,056,401.

Exemplary of additional prior art attempts to solve the problem are the following:

U.S. Pat. No. 2,710,001 which issued on June 7, 1955 to Freyburger teaches an automatically operated diastolic and systolic blood pressure indicating instrument which is designed to improve the sensitivity and accuracy of blood pressure readings, and employs two pressure gauges and an automatically operated switching means which senses the pulsation and blood pressure which occurs as the system pressure is released. This invention utilizes a complex system of relief and solenoid valves to achieve the pressurization of each of the two gauges in order to affect the reading of the systolic and diastolic pressures, respectively.

U.S. Pat. No. 3,929,129 which issued on Dec. 30, 1975 to Archambault is directed to a device for checking blood pressure involving the use of two pressure relief valves which are adapted to relieve pressure in an inflatable cuff at two different predetermined pressures, along with the necessary equipment for isolating the first pressure relief valve in order to allow the activation of the second pressure relief valve. The purpose of this system being to allow one to determine when he has either a moderate or a severe case of high blood pressure. The system taught does not allow one to precisely determine the systolic and diastolic pressure readings.

U.S. Pat. No. 4,007,734 which issued on Feb. 15, 1977 to Peters is directed to a blood pressure indicator adapted for self-examination which utilizes a pair of pressure sensing switches on the bladder of the inflatable cuff, which switches are set to either audibly or visually indicate when the maximum systolic or diastolic pressure permissible has been exceeded. Once again, this device does not allow one to accurately determine the pressure readings involved.

U.S. Pat. No. 4,010,739 which issued on Mar. 8, 1977 to Leach teaches a sphygmomanometer construction which incorporates into the pressure indicating gauge additional means for determining when the systolic and diastolic pressures have been reached without the necessity of utilizing a stethoscope or other electronic medium. This device while enabling one to easily determine the precise reading of the blood pressure of the subject, it involves the utilization of much more sophisticated and expensive equipment than that which is called for in the present invention.

U.S. Pat. No. 4,222,390 which issued on Sept. 16, 1980 to Berliner et al. is directed to a sphygmomanometer gauge with multiple indicators to allow one to manually fix the location on the gauge of the systolic and diastolic pressure readings which can then be recorded at a later time. While this is an improvement over the more complex embodiments taught by the prior art, it nevertheless requires the utilization of a more sophisticated and involved gauge construction which is not needed in the present invention.

The sphygmomanometer construction of the present invention allows one taking either their own or another's blood pressure to obtain a more accurate reading of the systolic and diastolic pressure readings by allowing the user to effectively isolate the individual pressure readings for a period of time, thereby enabling him to observe the reading on the pressure gauge which has been frozen at the appropriate moment by the activation of a normally closed, manually operated means which serves to momentarily pressurize and subsequently isolate the pressure gauge.

In the construction of the present invention, the pressure gauge is normally closed off from the ambient pressure in the inflated cuff and only senses the pressure upon the opening and subsequent closing of the manually operated means provided for, which distinguishes this invention over the prior art.

One employing the construction of the present invention would normally pressurize the cuff using the inflatable bulb provided, while checking the heartbeat in the normal fashion. In inflating the inflatable cuff no heartbeat would be detected until the cuff had exceeded the diastolic pressure and subsequently the detected heartbeat would disappear when the pressure in the cuff had exceeded the systolic pressure, at which time the user would be apprised to cease inflating and commence the depressurization sequence.

Upon again initially detecting the heartbeat, the user would manually operate the opening and closing means provided to momentarily expose the pressure gauge to the pressure reading in the cuff.

Such pressure reading would remain on the gauge, due to the fact that the gauge would, by operation of the opening and closing means, subsequently be isolated from the ambient pressure in the cuff, thereby fixing the pressure on the gauge until such time as the means was again manually operated when the user reaches the point of the diastolic pressure reading.

It will, therefore, be apparent that the pressure gauge in the sphygmomanometer construction of the present invention is not utilized in the normal sense as a continuous pressure detecting device but rather as a recording device which will only be affected when the normally closed, manually operated means is opened to allow the gauge to sense the ambient pressure in the inflated cuff.

It is, therefore, an object of the present invention to provide a sphygmomanometer construction which allows the user to easily and accurately determine his or her own or another's blood pressure readings without necessitating the utilization of complicated and expensive automatic equipment and/or other sophisticated devices, such as is required by the prior art.

It is also an object of the present invention to provide for a sphygmomanometer construction which is easily and cheaply assembled from standard components so as to diminish the cost of such devices to the user.

It is a further object of the present invention to provide for a sphygmomanometer construction which allows one to accurately determine systolic and diastolic pressure readings without the degree of uncertainty normally associated with the reading of a pressure gauge while simultaneously manipulating the various other components of a typical blood pressure apparatus.

It is yet another object of the present invention to provide for a simple device which can readily be incorporated into existing sphygmomanometers to permit the modification of existing constructions in order to allow them to operate in the manner provided for.

These and other objects of the present invention will become apparent from the following detailed description of an embodiment of the invention.

SUMMARY OF THE INVENTION

In accordance with the present invention, a sphgymomanometer is provided comprising in combination an inflatable cuff adapted to securely encircle a human limb;
a pump means connected to said inflatable cuff via a suitable conduit to affect the inflation thereof;
a manually operated pressure relief means; and
a pressure gauge interconnected to said inflatable cuff via a second suitable conduit having interposed in the interconnecting conduit between said pressure gauge and the point of interconnection with said inflatable cuff a normally closed, manually operated means for momentarily opening and closing the said second conduit thereby affecting the pressurization and subsequent isolation of said pressure gauge, in order to sense and maintain the pressure in the said inflatable cuff at the moment of opening and shutting of said means.

This invention also provides for a sphygmomanometer construction which allows one taking their own or another's blood pressure to obtain a more accurate reading of the systolic and diastolic pressure readings by allowing the user to effectively isolate the individual pressure readings, thereby enabling him to observe the reading on a pressure gauge which has been frozen at the appropriate moment by the activation of a normally closed, manually operated means which serves to momentarily pressurize and subsequently isolate the said pressure gauge.

DESCRIPTION OF THE PREFERRED EMBODIMENTS

Figure 1:
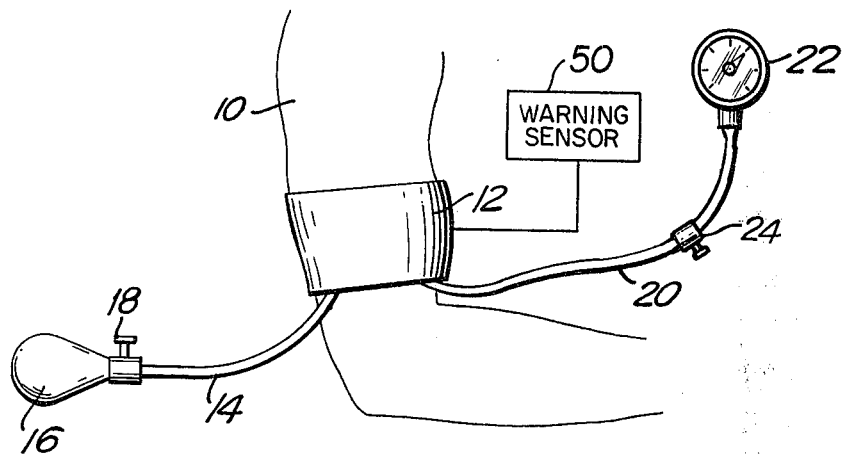
FIG. 1 illustrates a schematic representation of the components of one embodiment of the present invention, utilizing a single pressure gauge.

With reference to the drawings in which similar referenced characteristics denote similar elements, FIG. 1 shows a schematic representation of a limb 10, encircled by an inflatable cuff 12, to which is connected a conduit 14, at one end of which is a pump bulb 16, for inflating said cuff. A pressure relief valve 18, is provided in conjunction with the pump bulb 16, in order to affect the depressurization of the inflated cuff.

Also attached to said cuff is a second conduit 20, connected to which is a dial type pressure gauge 22. Interposed along the conduit 20, is a normally closed, manually operated valve 24, which is designed to operate in such a manner that the pressure gauge is normally isolated from the rest of the system.

Upon activation of the normally closed valve, pressure from the conduit 20, will be allowed to pressurize the gauge 22. Momentarily thereafter the normally operated valve 24, will revert to a closed position thereby again isolating the gauge 22, from the system and holding the pressure reading on the gauge.

During the normal operation of the sphygmomanometer depicted in FIG. 1, the user will, by applying a stethoscope to the brachial artery in the upper arm below the pressurized cuff, determine the point at which the systolic pressure reading should be taken in the normal fashion and at that point activate the manually operated valve so as to fix the pressure reading at that point on the said pressure gauge. The user may then leisurely record the reading on the pressure gauge as the systolic pressure without the disadvantage of having to make a rapid determination as to what the gauge reading should be while the system is in a dynamic state with the gauge needle falling through the point of the actual systolic pressure reading. Consequently, the disadvantage of having to estimate the point of such reading is avoided.

As the pressure in the system is further reduced and the user determines the point of diastolic pressure by similarly applying a stethoscope to the brachial artery, the manually operated valve is again momentarily achieved in order to again fix the pressure in the inflated cuff on the said pressure gauge. The user may then again leisurely record the reading for the diastolic pressure which has been fixed on the pressure gauge in the same manner as was done for the systolic pressure.

Figure 2:
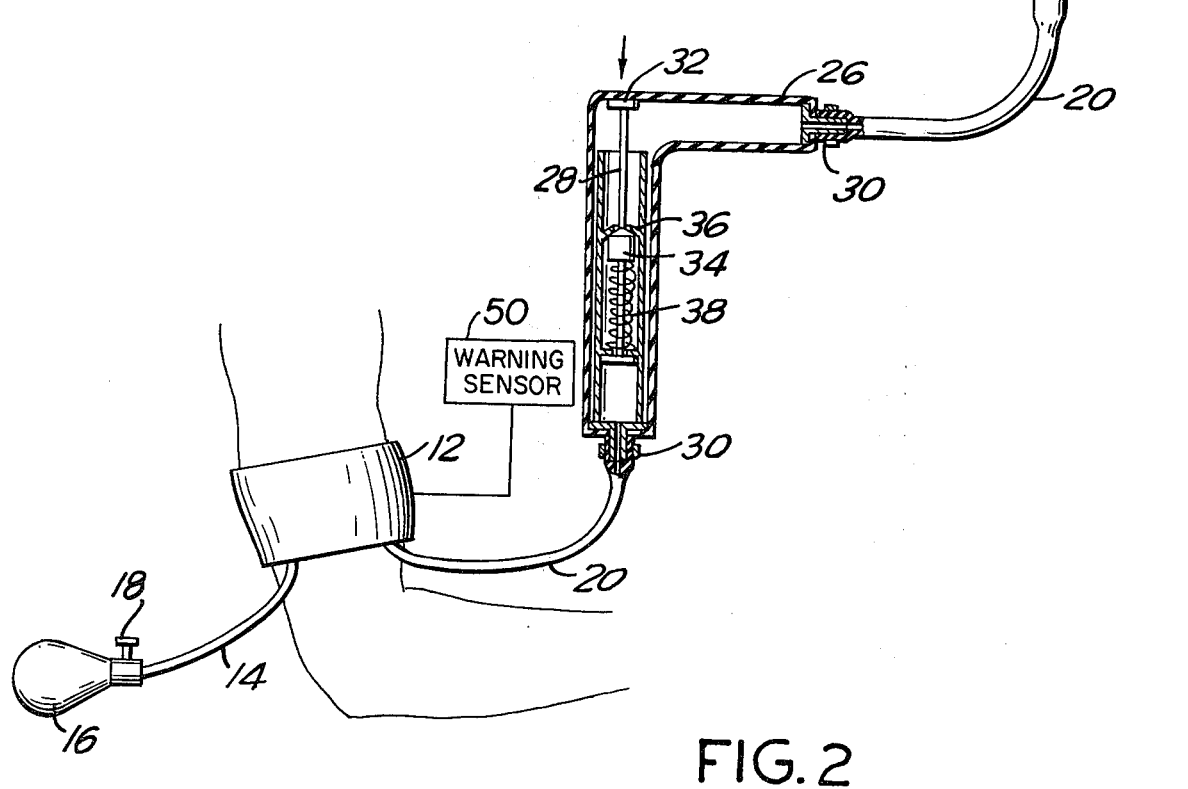
FIG. 2 illustrates one embodiment of a normally closed valve which may be effectively employed in carrying out the concept of the present invention.

With regard to FIG. 2, a preferred embodiment of the normally closed, manually operated valve is depicted. Interposed is conduit 20 is a L-shaped flexible tube 26, which is provided with a spring loaded plunger-type valve assembly 28, which is sealed within the said L-shaped tubing and which is normally in a closed position, the respective ends of the L-shaped flexible tubing containing the said normally closed plunger-type valve assembly are provided with protruding nipples 30, to which the respective portions of the conduit 20 may be easily attached.

The plunger-type valve assembly is provided with a plunger 32, which upon being manually depressed by the user opens the valve by dislodging the valve seat 34 from the mating surface 36, and momentarily exposes the upstream side of the conduit 20 and therefore the gauge 22, to the ambient pressure in the cuff 12. Upon release of the plunger 32 by the user, the valve seat returns to its normally closed position by the combined force of the spring 38, and the pressure in the conduit 20.

It is contemplated that the manually operated valve in the configuration of the present invention may be of the mechanical, electrochemical or electronically activated variety. The valve components themselves will be such as to enable the pressure gauge to be normally isolated from the pressure in the inflated cuff and upon activation will normally open to pressurize the gauges and equalize the pressure with that in the cuff and momentarily revert to the closed position in order to thereby fix the pressure on the gauge and isolate the gauge from the further effect of the diminishing pressure in the inflated cuff until such time as the manually operated valve is again activated.

It is also contemplated that the sphygmomanometer construction of the present invention may be provided with a means 50 for signalling either visibly or audibly the pressurization of the cuff and, consequently, of the exhaust conduit, above a predetermined fixed level so as to warn the user against the application of excessive pressure to the limb when inflating the cuff.

A preferred embodiment of the present invention has been illustrated and alternative arrangements have been described which will be effective to achieve the objects set forth. Other alternative construction arrangements including changes, modifications and substitutions of parts may be made as will be obvious to one skilled in the art without departing from the spirit of the invention.

I claim:

1. A sphygmomanometer construction comprising in combination:
    an inflatable cuff adapted to securely encircle a human limb;
    a pump means connected to said inflatable cuff via a suitable conduit to affect the inflation thereof;
    a manually operated pressure release means connected to said pump means; and
    a single pressure gauge for reading systolic and diastolic pressures interconnected to said inflatable cuff via a second suitable conduit having serially interposed in the interconnecting conduit between said pressure gauge and the point of interconnection with said inflatable cuff a normally closed, manually operated valve for momentarily opening and closing the second conduit thereby affecting the pressurization and subsequent isolation of said pressure gauge, in order to sense and maintain the pressure in said inflatable cuff at the moment of opening and shutting of said valve.

2. A sphygmomanometer construction according to claim 1 wherein the normally closed, manually operated valve is a mechanically activated device.

3. A sphygmomanometer construction according to claim 1 wherein the normally closed, manually operated valve is an electrically activated device.

4. A sphygmomanometer construction according to claim 1 wherein the normally closed, manually operated valve is an electrochemically activated device.

5. A sphygmomanometer construction according to claim 1, wherein a warning sensor is provided, said warning sensor being connected to said cuff and responsive to a preset maximum pressure for producing a signal when the pressure in said inflatable cuff increases beyond said preset pressure.

6. A sphygmomanometer construction according to claim 5 wherein the warning sensor emits an audible signal.

7. A sphygmomanometer construction according to claim 5 wherein the warning snesor displays a visual signal.

8. A sphygmomanometer construction according to claim 1 wherein the normally closed, manually operated valve is a spring loaded plunger-type valve arrangement which is sealed within an L-shaped section of flexible tubing wherein the said L-shaped section of flexible tubing is provided with a mating nipple at each end thereof for easy insertion within the second conduit connecting the pressure gauge and the inflatable cuff.

* * * * *

UNITED STATES PATENT AND TRADEMARK OFFICE
CERTIFICATE OF CORRECTION

PATENT NO. : 4,413,631
DATED : November 8, 1983
INVENTOR(S) : Harold G. Lacks

It is certified that error appears in the above—identified patent and that said Letters Patent is hereby corrected as shown below:

Column 5, line 24, change "achieved" to -- activated --.
Column 5, line 52, change "electrochemical" to -- electromechanical --.
Column 6, line 43, change "electrochemically" to -- electromechanically --.

Signed and Sealed this

Twenty-eighth Day of February 1984

[SEAL]

Attest:

GERALD J. MOSSINGHOFF

*Attesting Officer*  *Commissioner of Patents and Trademarks*